United States Patent [19]

Rauschenberger

[11] 4,160,505
[45] Jul. 10, 1979

[54] CATHETERIZATION TRAY

[75] Inventor: Richard A. Rauschenberger, Brookfield, Wis.

[73] Assignee: Will Ross Inc., Milwaukee, Wis.

[21] Appl. No.: 862,074

[22] Filed: Dec. 19, 1977

[51] Int. Cl.² ............................................. B65D 85/54
[52] U.S. Cl. ..................................... 206/571; 206/564
[58] Field of Search ............................... 128/348–351; 206/364, 370, 560–565, 570, 571

[56] References Cited

U.S. PATENT DOCUMENTS

| | | | |
|---|---|---|---|
| 2,319,556 | 5/1943 | Rhein | 206/570 X |
| 3,329,261 | 7/1967 | Serany, Jr. et al. | 206/364 X |
| 3,485,352 | 12/1969 | Pilger | 206/364 |
| 3,601,277 | 8/1971 | Andrews et al. | 206/564 X |
| 3,851,649 | 12/1974 | Villari | 206/571 X |

Primary Examiner—Davis T. Moorhead
Attorney, Agent, or Firm—John A. Dhuey

[57] ABSTRACT

A urethral catheterization tray providing a sterile, self-contained catheterization package and work area is described.

2 Claims, 3 Drawing Figures

CATHETERIZATION TRAY

This invention is concerned with catheterization trays. More particularly, it is concerned with a sterile, self-contained catheterization package which permits the catheterization procedure to take place within the sterile work area defined by the tray.

Prior art devices have generally employed a tray containing the catheterization implements, i.e. catheter, lubricant, antiseptic, absorbent material such as gauze or cotton, gloves, specimen container, towel and forceps, covered with a sterile folded central supply room (CSR) wrap. In use the CSR wrap is unfolded from the tray to provide a sterile work area about the tray, the area taken up by the extended wrap generally being 1-2 square feet. The attending person then dons the rubber gloves, extracts a lubricant packet from the tray and places an amount of lubricant on the CSR wrap. Next the absorbent pads contained in a cup are removed from the tray by means of the forceps and placed on the wrap. Antiseptic solution then is applied to the pads and the patient is cleansed. Remaining dry absorbent pads then are utilized to dry the patient. The catheter is removed and the insertion end placed into the lubricant on the wrap and inserted into the patient. When catherization is completed, the specimen container is removed from the tray and placed on the wrap. Then a specimen from the bag is allowed to drain onto the container.

It is apparent from the above outlined procedures that less than ideal circumstances are created. For example, the large area taken up by the CSR wrap necessitates a large work area near the patient. Such a substantial area must usually be found on the bed where indavertent movement by the patient could contaminate the sterile work area. During the procedure lubricant jelly, antiseptic solution, and wet absorbent pads are placed on the CSR wrap, where they can be contacted either by the patient or the attending personnel. Furthermore, the chances of spilling urine when attempts are made to fill the specimen container are substantial and soiling of the immediate area is a distinct and unpleasant possibility.

The present invention is intended to eliminate the above-noted deficiencies and is best understood with reference to the following drawings in which.

Figure 1:
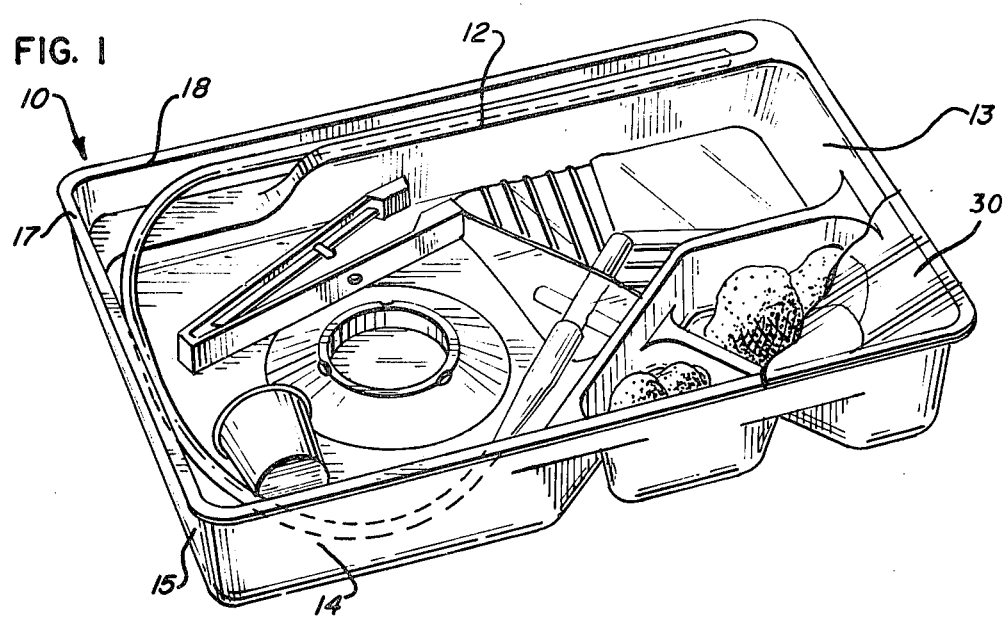
FIG. 1 is a perspective view of the assembly.
Figure 2:
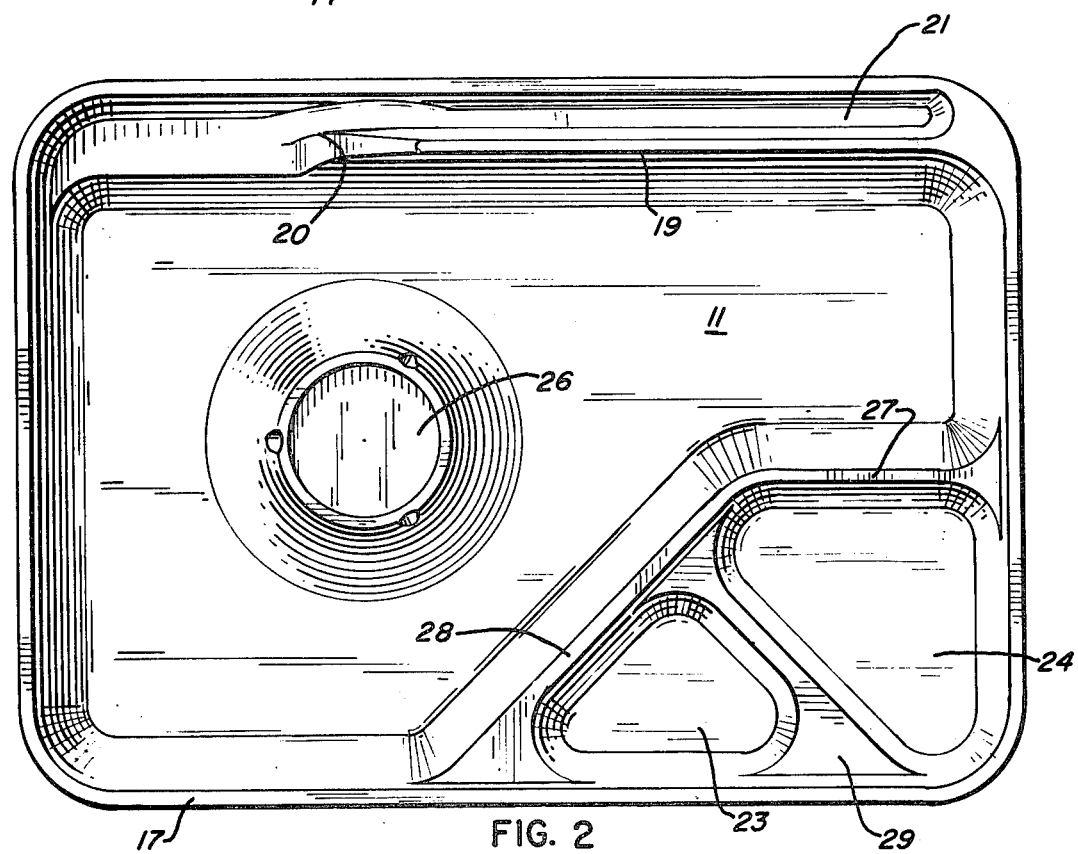
FIG. 2 is a topview of the tray.
Figure 3:
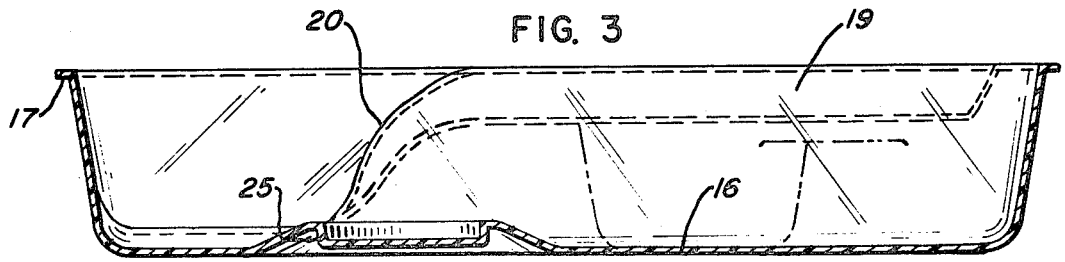
FIG. 3 is a cross-sectional view of the tray.

Tray 10 is formed with a dished portion 11 defined generally by outside walls 12, 13, 14, 15 and 18 and bottom wall 16. The top edge of walls 12, 13, 14, 15 and 18 are integral with a flange 17 which extends about the periphery of tray 10. Walls 12 and 18 jointly form one full outside wall on tray 10 and wall 12 is inset from wall 18 and the outer edge of flange 17. Flange 17 and wall 12 are connected by a channel 21 which has a horizontal section 19 and an inclined section 20 forming a ramp. Wall 12 correspondingly is inclined in the area of secton 20 and cooperates with wall 18 to form the channel 21 in that portion of dish 11.

Channel 21 is adapted to receive a conventional urethral catheter which is positioned within channel 21 with its insertion end in the horizontal section. The remainder of the catheter extends down the ramp section 20 and around the sides of dish 11. Channel 21 optionally can be provided with a cross-channel in its horizontal section.

Compartments 23 and 24 are defined within dish 11 by walls 27, 28 and 29. Those walls are conveniently formed by directionally varying outside wall 14. Since the tray 10 usually will be molded as a unit structure, such variations present no problem. Compartments 23 and 24 are independent and adapted to hold absorbent pads separately from each other.

A further compartment in the tray is provided by wall 25 which creates a generally circular compartment 26 in the bottom of dish 11. Conveniently wall 25 is formed by dropping bottom wall 16 appropriately to provide recess 26. Again, fabrication is facilitated by the molding operation which permits direct formation of wall 25.

In its packaged configuration the catheterization implements are placed in tray 10 as shown in FIG. 1 and sealed with a cover sheet 30 about flange 17. Cover sheet 30 is formed of conventional peelable lid stock such as coated paper or plastic which is permeable to sterilizing gases. The catheter is located in groove 21 and absorbent material is located in compartments 23 and 24. The remaining componetns generally are arranged sequentially from the top of the tray on down in the order: gloves, lubricant, antiseptic solution, fenestrated drape, forceps, drainage bag and specimen container. For purposes of clarity, not all of the components are shown in the drawings.

In use the attendant places the tray at a convenient location. The seal lid then is removed and discarded. Gloves are donned and a lubricant packet is utilized to put lubricant on the catheter in channel 21. The catheter then is rotated within channel 21 to spread lubricant about it insertion end. Ramp section 20 supports the catheter during its rotational movement and minimized the danger of the catheter being dislocated from channel 21. If the optional cross channel has been provided, the attendant's finger may be placed in cross-channel to further hold the catheter within groove 21 and also assist in rotation. It has been found that the most preferred manner is to grasp the catheter near the bottom of ramp 20 and rotate the catheter between the finger and the thumb.

After the catheter has been lubricated, antiseptic solution is applied to the absorbent pads in one, but not both, of the compartments 23 and 24. Since compartments 23 and 24 are independent, the saturation of one set of absorbent pads does not affect the other set. Then the fenestrated drape is removed from tray 10 and placed over the patient area. Next the patient is cleansed with the saturated absorbent pads by holding with the forceps. The remaining dry pads subsequently are used to dry the patient. Both sets of pads and the tweezers, along with the empty packets are discarded after use. Conveniently, they are placed in the compartments 23 and 24 which are no longer needed. The patient is catheterized and the urine collected in the drainage bag. While the urine is being collected, the specimen container is opened and placed upright in recess 26, which is sized appropriately to receive and stabilize it. After the urine has been collected, a sample is removed from the bag into the upstanding container. It is noted that any spillage which occurs will be directed into tray 10 and not contaminate the surrounding area.

Although the invention has been described with reference to the drawings, they are presented as illustrations of preferred embodiments of the invention and not meant to limit the invention either in spirit or in scope.

What is claimed is:

1. A catheterization tray providing a sterile, self-contained catheterization package and work area comprising:
   a generally rectangular dish having a bottom, four upstanding side walls and a continuous outwardly extending flange integral with the top of said walls,
   at least two independent compartments within said dish for separately retaining absorbent material in each compartment;
   a wall on the bottom of said dish defining a circular recess for receiving and holding upright a specimen container;
   a raised wall section in said dish extending substantially the length of said dish and having a horizontal portion and an inclined portion;
   a channel adapted to receive a catheter located in the top of said raised wall and extending substantially the length of said horizontal and inclined portions; and
   a releasable cover sheet sealed to said flange, said cover sheet being permeable to sterlizing gases.

2. A catheterization package providing a sterile, self-contained work area comprising:
   a generally rectangular dish having a bottom, four upstanding side walls and a continuous outwardly extending flange integral with the top of said walls;
   at least two independent compartments within said dish for separately retaining absorbent material in each compartment, said compartments being adjacent to each other and separated by a wall preventing fluid flow therebetween;
   a wall on the bottom of said dish defining a circular recess for receiving and holding upright a specimen container;
   a raised wall section in said dish extending substantially the length of said dish and having a horizontal portion and an inclined portion;
   a channel for receiving a catheter located in the top of said wall and extending substantially the length of said horizontal portion; and
   a releasable cover sheet sealed to said flange, said dish containing a catheter at least partialy located within said channel, gloves, lubricant, antiseptic solution, drape, forceps, drainage bag, specimen container adapted to be retained in an upright position in said recess, and absorbent material in each of said independent compartments.

* * * * *